United States Patent
Friedman

(10) Patent No.: US 6,632,843 B1
(45) Date of Patent: Oct. 14, 2003

(54) TREATMENT OF BRUXISM

(76) Inventor: Mark Friedman, 5 Forest Ct., Larchmont, NY (US) 10538

( * ) Notice: Subject to any disclaimer, the term of this patent is extended or adjusted under 35 U.S.C. 154(b) by 0 days.

(21) Appl. No.: 09/495,690

(22) Filed: Feb. 1, 2000

(51) Int. Cl.[7] .................. A61K 31/13; A61K 31/19; A61K 31/55
(52) U.S. Cl. .................. 514/662; 514/78; 514/570; 514/221; 514/681; 514/944
(58) Field of Search .................. 424/437; 514/649, 514/650, 656, 662, 679, 681, 944–947, 570, 221, 78

(56) References Cited

U.S. PATENT DOCUMENTS 4,065,561 A * 12/1977 Gassel
4,934,378 A *  6/1990 Perry
5,654,337 A *  8/1997 Roentsch

* cited by examiner

*Primary Examiner*—Gollamudi S. Kishore
(74) *Attorney, Agent, or Firm*—Evelyn M. Sommer

(57) ABSTRACT

This invention relates to the use of a composition for local percutaneous delivery of a drug such as a muscle relaxant, more particularly cyclobenzaprine in an organogel cream. The composition is applied by the patient directly to the skin over accessible muscles of mastication i.e., masseter and temporalis. The composition is rapidly absorbed through the skin to provide control of harmful habits such as bruxism and tooth clenching. The composition can also be applied to the skin overlying these muscles to control muscle hyperactivity (spasm) and/or trigger points, from other causes. The composition can be formulated to include another active agent such as a non-steroidal anti-inflammatory, for example ketoprofen. The advantage of topical administration versus systemic include use of lower doses of drug, delivery of the drug to the desired site, avoidance of the gastrointestinal tract and hepatic first-pass biotransformation and metabolism, and elimination of many of the side effects of the drug normally associated with systemic administration.

10 Claims, 4 Drawing Sheets

(4 of 4 Drawing Sheet(s) Filed in Color)

TREATMENT OF BRUXISM

This invention relates to the use of a composition for the local percutaneous delivery of at least one pharmaceutically active agent formulated in a lecithin organogel cream.

In the preferred embodiment of the invention, the composition is formulated with the muscle relaxant, cyclobenzaprine. The composition is applied by the patient, directly to the skin, over accessible muscles of mastication (masseter and temporal is). Such a composition is rapidly absorbed through the skin to provide control of muscle tension and relief from pain resulting from bruxism (tooth grinding) and tooth clenching (isometric muscle contraction). Similarly a composition can be formulated comprising an additional pharmaceutically active agent such as a non-steroidal anti-inflammatory drug such as ketoprofen or other similarly active agent. Other pharmacologically active substances can also be added, for example an anti-anxiety compound such as diazepam.

Bruxism (tooth grinding when not masticating or swallowing) and tooth clenching, ( that is isometric muscle contraction with the teeth in contact) common of the functional jaw disturbances. The isometric contraction produced during clenching is even more tiring to the muscles than the isotonic contraction produced during bruxism. However, bruxing forces are still considerable. The volume of the sound produced during grinding is considerable and is difficult to simulate voluntarily. This excitation of the jaw closing muscles appears to serve as a tension-relieving mechanism. Some individuals are more susceptible to environmental stress, and respond by increased jaw muscle tension, either at night of with day time clenching. It has been postulated that the protective mechanism in these individuals has been dulled down. Experimental evidence has shown that in addition to discomfort, damage accompanies such muscular hyperactivity.

Para-functional oral habits, particularly bruxism, and tooth clenching as well as myofacial pain are common components of temporomandibular joint (TMJ) dysfunction. TMJ disorders are estimated to affect from 10 to 30 million Americans with approximately one million new patients diagnosed yearly. The majority of TMJ sufferers are women, ages 20 to 40. It has been demonstrated that tooth clenching or tooth grinding in response to stressful life situations is associated with or may actually induce depression, anxiety, frustration and chronic pain. These symptoms are more marked in patients with TMJ problems than in control subjects. The regular repetitive side-to-side tooth contacts of bruxism differ from the haphazard pattern observed during mastication. Bruxism or clenching at night is often totally beyond the patient's awareness. A classic presentation is pain in front of and just below the tragus, with radiation to the ear, lower jaw, cheek and temple. Pain is usually worse in the morning and may occur in cyclical episodes. In response to questioning, these individuals often describe (1) orofacial or jaw pain and other symptoms on arising, (2) posterior tooth soreness on arising, (3) teeth pressed together on awakening, and (4) jaw "tiredness" during chewing. Typical wear facets and/or worn teeth can be seen in strong bruxers, but not in those who clench. Nocturnal monitoring of masseteric electromyographic (EMG) activity in bruxers showed marked increases of EMG activity (bruxism) during periods of life situational stress. These habits abuse the masticatory muscles, especially the masseter, and result in muscle dysfunction, i.e. muscle spasm and trigger points. Muscle spasm is the commonest manifestation of musculoskeletal pathology, and can be defined as a prolonged continuous contraction of muscle. Trigger points are small, ischemic, tender points in the involved muscle and its associated area caused by abnormal functioning (overloading) of the muscle. The trigger points can refer pain and other symptoms, especially jaw "tiredness". Trigger points are undetectable by the usual muscle tests, such as application of maximal resistance to the muscle. Muscles in spasm respond to these tests by demonstrating pain or other symptoms. Due to a lowered skin resistance (impedance) over the point, trigger points can be verified by various electronic detectors. In addition to referring pain, they perpetuate muscle tenderness, and prevent full muscle lengthening (relaxation). In bruxers or clenchers, multiple trigger points are most always found in the deep vertical fibers of the masseter muscle, just under the tempromandibular joint, and often in the posterior belly of the digastric and stylohyoid muscles, anterior and inferior to the ear lobe(s). Trigger points in these muscles often refer symptoms, such as congestion, pain, and tinnitus to the ears, as well as swallowing difficulties, i.e., eustachian tube dysfunction. This is often confusing, since, in these cases, objective signs of car dysfunction are absent.

Bruxism and/or clenching can be initiated by systemic, psychological, occupational and occlusal factors. Often, a combination of general and local factors influencing each other, set up a vicious cycle. Standard treatment for the above parafunctional habits generally consists of one or more of the following: physical therapy and namely prescribed exercises, massage, application of moist heat, or cold in the form of ice packs, behavior modification, medication taken orally including non-steroidal anti-inflammatories, muscle relaxants, tricyclic antidepressants, tranquilizers or anti-anxiety drugs. Behavior modification, with stress reduction as its goal, generally consists of counseling on life style and relaxation therapy and/or biofeedback Biofeedback uses equipment to measure biologic activity, e.g., surface electromyography to measure muscle activity. A "feed back loop" allows the patient to receive immediate information (feedback). The patient, guided by this information, is then trained to reduce excessive muscular activity by appropriate thought processes. Control of bruxism or clenching by medication usually involves muscle relaxants, such as diazepam or cyclobenzaprine. These medications when taken orally are associated with side effects; particularly sedation, but dependency, in the case of diazepam can be a problem. Other prescribed medications resembling muscle relaxants, such as Esgic (butalbital, acetaminophen and caffeine), have generalized depressive effects on the central nervous system and can be addictive.

Removable dental appliances are commonly prescribed to control or eliminate these harmful oral habits. These appliances, usually designed with flat occlusal surfaces, fit over the maxillary or mandibular teeth to prevent complete closure; since the powerful jaw closing muscles (masseter, temporalis, medial pterygoid) cannot shorten completely, they cannot contract as forcefully. Additionally, the flat occlusal surface eliminates the usual triggers, abrasive contact between irregular tooth surfaces.

Occlusal adjustments, elimination of perceived excessive tooth contact by grinding, may be effective. However if incorrect surfaces are removed, the situation may worsen. Unlike appliances, which can be modified by adding or subtracting plastic, elimination of tooth surface is irreversible.

BRIEF DESCRIPTION OF THE DRAWINGS

The file of this patent contains at least one drawing executed in color. Copies of this patent with color drawings are provided to the Patent and Trademark Office with Payment of the necessary fee.

SUMMARY OF THE INVENTION

Figure 1:
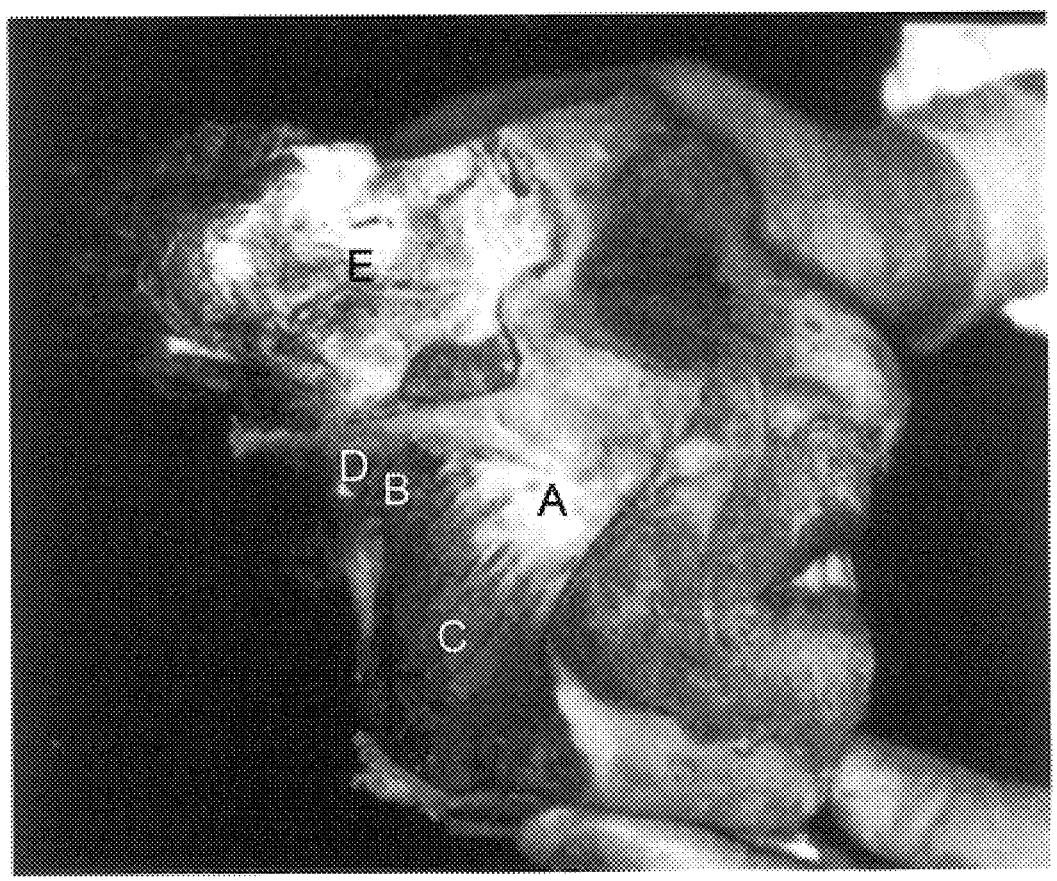
FIG. 1 illustrates the lateral aspect of the masseter muscle.

This invention relates to the use of compositions containing pharmaceutically active agents to be used for the treatment of temporomandibular disorders, including bruxism tooth grinding, tooth clenching and various car symptoms including, congestion, swallowing difficulties, tinnuitis, and pain referred from adjacent muscles. In accordance with the invention the compositions are applied topically onto the intact skin for local subcutaneous delivery of a muscle relaxant, namely cyclobenzaprine. Compositions comprising more than one active agent are within the scope of this invention and could be administered to a patient who might benefit from the differing properties of such a formulation. Thus the composition may be formulated to comprise other pharmaceutically active agents in addition to the muscle relaxant. Such agents include a non-steroidal anti-inflammatory, preferably ketoprofen, or an anxiolytic agent such as diazepam. The composition, formulated as a cream using lecithin organogel as the delivery vehicle, is applied by the patient onto the intact skin overlying accessible muscles of mastication, i.e., masseter, temporalis. Similarly application of the composition to these or other muscles may be used to control muscle spasm or hyperactivity. It may be applied to tender spots known as trigger points in the involved muscle and associated area. Once the formulations have been prepared, use of the composition is a simple matter of applying the formulation to the affected areas where transdermal delivery of the pharmaceutically active agent(s) is desired. The amount of cream applied, about one gram, is used to cover an area the size of two fingers (about one inch by two inches). The advantages of topical administration include use of lower doses of active agents, avoidance of the gastrointestinal tract and hepatic first by-pass biotrans formation and metabolism, and delivery of the drug to the a specific area (local) versus systemic distribution of the drug.

The compositions for transcutaneous delivery of pharmaceutically active agent(s) are formulated in organogel this gel comprises a biocompatible organic solvent, a polar lipid, a biocompatible surfactant, water, urca and the pharmaceutically active substance(s). The polar lipid is preferably lecithin, the biocompatible organic solvent is preferably isopropyl myristate and the surfactant preferably is docusate sodium. Preferred composition comprise preferably lecithin 10–30%, isopropyl myristate 10–30%, urea 5–20%, water 30–60% and surfactant 10–20%. After formulation of the composition with the pharmaceutically active agent, and adjustment of the pH to the desired range, the formulation thickens and forms a gel suitable for topical administration. The final pH should be in the range Of 6.0 to 7.0 . The appropriate pH is obtained by adjusting with aqueous NaOH. Depending on the chemical properties, for example the solubility characteristics of the pharmaceutically active agent the steps in compounding the composition may vary slightly. Some agents may require some heating before a consistent mixture may be achieved. The active compound is added to the mixture of the polar lipid and organic solvent. The mixture may be warmed before adding the active compound if required for solubilizing the active agent. Thorough mixing is accomplished by stirring.

Cyclobenzaprine HCI (.Flexeril, Merck) relieves muscle spasm of local origin without interfering with muscle function. There is a similarity between the effects of cyclobenzaprine and the structurally related tricyclic anti-depressants e.g. amitryptyline. Cyclobenzaprine is a 5-HT2 receptor antagonist and its muscle relaxant effect is due to inhibition of serotonergic neurons. Cyclobenzaprine significantly improves the signs and symptoms of skeletal muscle spasm. The clinical response includes improvement in local pain and tenderness and increased range of motion. Clinical improvement is often observed as early as the first 20 minutes of application. When taken orally, cyclobenzaprine is eliminated slowly with a half life as long as one to three days it is highly bound to plasma proteins, is metabolized primarily to glucuronide like conjugates and is excreted, primarily through the kidneys. First pass metabolism is avoided by topical administration Diazepam (Valium Roche) which can be given concomitantly with Flexeril is indicated for the management of anxiety disorders or for the short-term relief of the symptoms of anxiety, or tension associated with stress. It is a useful adjunct for the relief of skeletal muscle spasm.

Ketoprofen (Orudis Wyeth) is another example of a drug which can be co-administered with Flexeril a non-steroidal anti-inflammatory drug with analgesic and antipyretic properties. Ketoprofen has been shown to have inhibitory effects on prostaglandin and Icukotriene synthesis, to have anti-bradykinin activity as well as to have lysosomal membrane stabilizing activity. When taken orally the drug is bound to plasma proteins and is excreted in the urine mainly as glucuronide like conjugates.

Formulations containing the above agents would be prepared so that cyclobenzaprine would be present in an amount of 0.5–1.0%, ketoprofen 5.0–10%, in addition to the cyclobenzaprine (0.5–1.0%), and diazepam 0.5–1.0% in addition to cyclobenzaprine (0.5–1.0%).

The composition (organogel plus the pharmaceutical active agent) is applied by the patient, usually at bed time; it can be used at other times of the day if necessary. The usual area of application is roughly that covered by two fingers, (an area of about one inch by two inches) and the amount of composition delivered would be about 1 ml (about one gram of composition).

In trials where the composition (cyclobenzaprine plus organogel) was applied in a controlled setting, sixteen out of twenty patients reported positive response within 20–25 minutes. In over 200 patients where the cream was prescribed, positive responses (within a few applications) have been reported by approximately 70% of the patients., with no side effects reported. Research has demonstrated minimal systemic effects from topical application of muscle relaxants and anti-inflammatory medications.

A BRIEF DESCRIPTION OF THE DRAWINGS

The drawings serve to illustrate the anatomical relationship of the facial muscles.

FIG. 1 shows the lateral aspect of the masseter muscle after removal of the superficial structures (superficial lobe of the parotid gland, parotid duct, buccal fat pad, muscular branches of the facial nerve). This muscle is the most powerful and most superficial of the muscles of mastication. The broad superficial part originates from a tendinous aponcurosis (a broad, flat tendon) attached to the zygomatic bone and zygomatic arch (1A). (C) represents the muscle belly.

The smaller deep posterior part (B) runs more vertically, and is attached directly to the zygomatic arch through short tendinous fibers. This section is often tender, with multiple trigger points in individuals who brux or clench.

Figure 2:
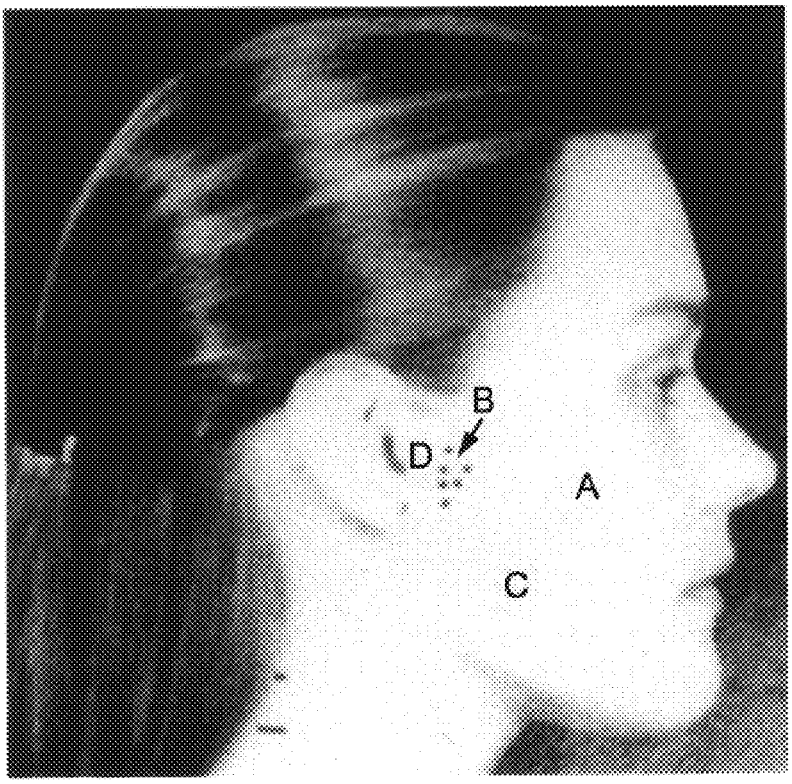
FIG. 2 illustrates the areas evidencing tenderness in a patient.

FIG. 2 shows the areas in a patient.

Figure 3:
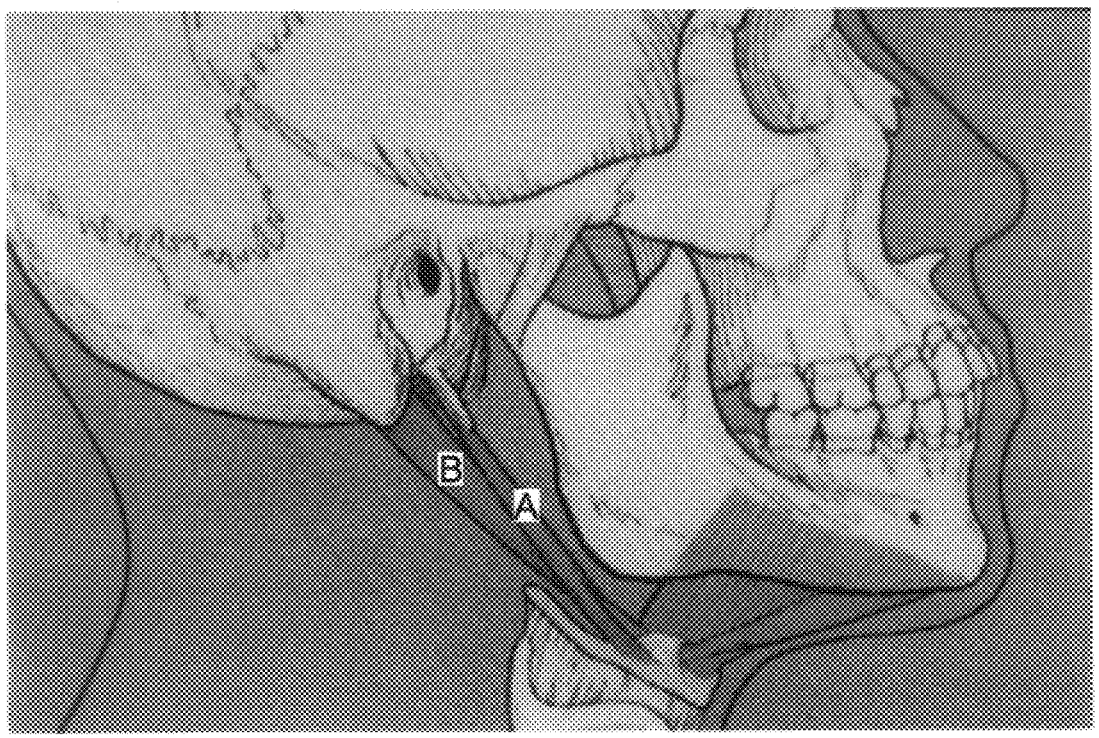
FIG. 3 illustrates the anatomy of the digastric muscle.

FIG. 3 shows the stylohyoid (A) and posterior belly of the digastric muscles(B).

Figure 4:
FIG. 4 illustrates the area of treatment in a patient.

In FIG. 4, the upper finger lies over the deep vertical masseter fibers, the lower finger lies over the stylohyoid (3A) and posterior belly of the digastric muscles (3B)—the usual area of application.

I claim:

1. A method for treating tooth grinding and tooth clenching in a patient having such condition which comprises topically applying directly to the skin overlying accessible muscles of mastication for absorption through the skin a therapeutically effective amount of a composition comprising cyclobenzaprine in a pharmaceutically acceptable carrier wherein said carrier is an organogel cream comprising lecithin, isopropyl myristate, urea, a surfactant and water.

2. Method according to claim 1 wherein said composition additionally contains at least one nonsteroidal anti-inflammatory drug.

3. Method according to claim 2 wherein said nonsteroidal anti-inflammatory drug is ketoprofen.

4. Method according to claim 1 wherein said composition additionally contains an anti-anxiety drug.

5. Method according to claim 4 wherein said anti-anxiety drug is diazepam.

6. Method according to claim 1 wherein said composition is applied in an amount of about gram to a skin area of about 1 to 2 inches.

7. Method according to claim 1 wherein said cyclobenzaprine is present in an amount of about 0.5–1%.

8. Method according to claim 10 wherein said cyclobenzaprine is present in an amount of about 0.5–1%.

9. Method according to claim 8 wherein ketoprofen is additionally present in an amount of about 5.0–10%.

10. Method according to claim 8 wherein diazepam is additionally present in an amount of 0.5–1%.

* * * * *